United States Patent [19]
Amigo

[11] Patent Number: 5,935,401
[45] Date of Patent: Aug. 10, 1999

[54] SURFACE MODIFIED ELECTROPHORETIC CHAMBERS

[75] Inventor: M. Goretty Alonso Amigo, Santa Clara, Calif.

[73] Assignee: Aclara Biosciences, Hayward, Calif.

[21] Appl. No.: 08/715,338

[22] Filed: Sep. 18, 1996

[51] Int. Cl.[6] .......................... G01N 27/26; G01N 27/447
[52] U.S. Cl. ........................ 204/454; 204/601; 427/393.5
[58] Field of Search ..................................... 204/451, 452, 204/453, 454, 455, 601, 602, 603, 604, 605; 427/412.1, 412.3, 412.4, 412.5, 385.5, 393.5, 498, 512; 428/34.7, 133

[56] References Cited

U.S. PATENT DOCUMENTS

| | | | |
|---|---|---|---|
| 4,472,480 | 9/1984 | Olson | 427/393.5 X |
| 4,600,201 | 7/1986 | Lönne et al. | 427/385.5 X |
| 5,039,549 | 8/1991 | Nguygen et al. | 427/393.5 X |
| 5,447,617 | 9/1995 | Shieh | 204/454 |

FOREIGN PATENT DOCUMENTS

| | | |
|---|---|---|
| 0 452 055 B1 | 1/1995 | European Pat. Off. . |
| 0 665 430 A1 | 8/1995 | European Pat. Off. . |

OTHER PUBLICATIONS

Schützner & Kenndler, "Electrophoresis in Synthetic Organic Polymer Capillaries: Variation of Electroosmotic Velocity and ζPotential with pH and Solvent Composition," Anal. Chem. (1992) 64: 1991–1995. No month available.

Nielen, "Capillary Zone Electrophoresis Using a Hollow Polypropylene Fiber," J. High Resolution Chrom. (1993) 16:62–64. No month available.

Hjertén "High Performance Electrophoresis Elimination of Electroendosmosis and Solute Adsorption," J. Chromatogr. (1985) 347:191–198. No month available.

Encyclopedia of Polymer Science and Engineering, "Adhesion and Bonding," vol. 1, p. 476 (Wiley Interscience , 1985). No month available.

*Primary Examiner*—William H. Beisner
*Assistant Examiner*—John S. Starsiak, Jr.
*Attorney, Agent, or Firm*—Flehr Hohbach Test Albritton & Herbert LLP

[57] ABSTRACT

Electrophoretic chambers comprising at least a region of surface modification, and methods for their fabrication, are provided. The subject chambers comprise in the region of surface modification, an anchoring polymeric layer interpenetrating the surface of the chamber and an electrophoretic polymeric layer copolymerized with the anchoring polymeric layer. The subject chambers are prepared by sequentially contacting the chamber surface with a first monomer capable of interpenetrating the surface and a second monomer capable of copolymerization with the first monomer, followed by copolymerization of the first and second monomers. The subject devices find use a variety of electrophoretic applications in which entities are moved through a medium under the influence of an applied electric field.

37 Claims, No Drawings

SURFACE MODIFIED ELECTROPHORETIC CHAMBERS

FIELD OF THE INVENTION

The field of this invention is electrophoresis.

1. Background of the Invention

Electrophoresis, in which entities are moved through a medium as a result of an applied electric field, has become an increasingly indispensable tool in biotechnology and related fields. In electrophoresis, the electrophoretic medium through which the entities are moved is housed in an electrophoretic chamber. A variety of different chamber configurations find use, including slab gel holders, columns or tubes, microbore capillaries, grooves or channels on a substrate surface etc., where advantages and disadvantages are associated with each particular configuration.

The particular material from which an electrophoretic chamber is fabricated can have a significant impact on the results of the application in which the chamber is employed. Some materials, e.g. fused silica, have charged surfaces under conditions of electrophoresis which give rise to electroosmotic flow. The presence of electroosmotic flow (EOF) can change the movement profile of the entities through the medium during electrophoresis. Certain materials can also adsorb entities from the medium, such as proteins and other biomolecules, which can adversely affect the results of a particular application.

As knowledge of the effect of surface properties on the movement of entities through a medium in electrophoretic applications grows, there is an increasing interest in the development of methods to tailor the surface properties of the electrophoretic chamber to meet the needs of a particular application. For example, it may be desirable to have a surface modified to reduce or enhance EOF through the chamber, to reduce or enhance analyte adsorption to the walls of the chamber, to provide for stable attachment of a gel network to the surface of the chamber, and the like.

Although fused silica has traditionally been the material of choice from which electrophoretic chambers are fabricated, of increasing interest as an alternative material are plastics. Various means have been developed for the surface modification of materials employed in electrophoretic applications. Surface modification techniques that have been employed include techniques based on the physical or chemical alteration of the material surface, e.g. etching, chemical modification, and coating a new material over the existing surface, e.g. solvent coating or thin film deposition by chemical or vapor deposition, radiation grafting, chemical grafting and RF-plasma. The particular surface modification means employed necessarily depends on the material to be modified. For methods specifically directed to the treatment of plastic surfaces of electrophoretic chambers, see EP 665 430 A1 and EP 452 055 B 1.

Despite the availability of a number of different plastic surface modification protocols, there is a continued interest in the development of new surface modification procedures which would increase the number of different available methods and provide for further surface property tailoring opportunities to best meet the needs of a particular application.

2. Relevant Literature

U.S. Pat. No. 4,680,201 reports a method for covalently attaching a polyacrylamide surface layer to the inner surface of fused silica capillaries. U.S. Pat. No. 5,433,898 reports a process for preparing material for use in the preparation of contact lenses comprising two or more polymers. EP 665 430 A1 and EP 452 055 B1 report the use of surface modified polymeric capillaries in electrophoresis.

Additional references reporting electrophoresis in various surface modified capillaries include: Gilges et al., "Capillary Zone Electrophoresis Separations of Basic and Acidic Proteins Using Poly(vinyl alcohol) Coatings in Fused Silica Capillaries," Anal. Chem. (1994) 66: 2038–2046; Rohlicek et al, "Determination of the Isoelectric Point of the Capillary Wall in Capillary Electrophoresis, Application to Plastic Capillaries," J. Chrom. A. (1994) 662: 369–373; Schützner & Kenndler, "Electrophoresis in Synthetic Organic Polymer Capillaries: Variation of Electroosmotic Velocity and $\zeta$ Potential with pH and Solvent Composition," Anal. Chem. (1992) 64: 1991–1995; Nielen, "Capillary Zone Electrophoresis Using a Hollow Polypropylene Fiber," J. High Resolution Chrom. (1993) 16: 62–64; and Liu et al., "Polymeric Hollow Fibers for Capillary Electrophoresis," J. Microcol. September (1993) 5: 245–253; Hjertén, "High Performance Electrophoresis Elimination of Electroendosmosis and Solute Adsorption," J. Chromatogr. (1985) 347:191–198.

Encyclopedia of Polymer Science and Engineering, "Adhesion and Bonding," Vol. 1, pg. 476 (Wiley Interscience, 1985) describes reactive adhesives based on the surface interpenetration of reactive monomers.

A review of the surface modification of polymer materials is provided in Ratner, Biosensors & Bioelectronics (1995) 10: 797–804.

SUMMARY OF THE INVENTION

Electrophoretic chambers having at least a region of surface modification, as well as methods for their fabrication, are provided. The region of surface modification comprises an electrophoretic polymeric layer, which provides for the tailored surface properties in the modified region, stably bound to the polymeric material of the chamber through copolymerization with an anchoring polymeric layer that interpenetrates the surface of the chamber. The subject chambers are prepared by contacting the surface of the chamber with a first monomer capable of interpenetrating the surface. The resultant interpenetrated surface is then contacted with a second monomer, followed by copolymerization of the first and second monomers. The subject devices find use in a wide variety of electrophoretic applications in which entities are moved through a medium in response to an applied electric field.

DESCRIPTION OF THE SPECIFIC EMBODIMENTS

Electrophoretic chambers having at least one region of surface modification, as well as methods for their fabrication, are provided. In the region of surface modification, where the term region encompasses anywhere from the entire inner surface of the chambers to only a fraction thereof, the chambers comprise a rigid polymeric base material, an anchoring polymeric layer penetrating the surface of the base material and an electrophoretic polymeric layer, which provides the tailored surface properties, copolymerized with the anchoring polymeric layer. In further describing the subject invention, the chambers will first be described in greater detail followed by a discussion of the methods used to fabricate the subject chambers.

In the subject chambers, at least that portion of the chamber in the region of surface modification will be fabricated from a solid, rigid polymeric material that is insoluble in aqueous media. As the polymeric material is solid and rigid, it will have sufficient strength to serve as a mechanical support for an electrophoretic medium, such as a buffer or gel. Although only the material in the region of surface modification will necessarily be the rigid, solid polymeric base material, the entire chamber, e.g. capillary or planar substrate having a microchannel on its surface, may be fabricated from the base polymeric material. Alternatively, the chamber may be fabricated from two or a plurality of different materials, so one has a chamber fabricated from a composite material. For example, in the walls of the chamber the base polymeric material can be present over a layer of another material, where the different material may serve to modify the physical properties of the substrate. Where desired, the second material present in the composite substrate may be a heat dissipating material which serves to absorb heat produced in the electrophoretic medium during electrophoresis. Materials that provide for heat absorption and dissipation and may be present in a composite substrate include glasses, ceramics, metals and the like. Specific heat absorbent materials of interest, depending on the nature of the microchannel, include aluminum, copper, glass and the like. Where the base polymeric material is a composite, the layer of rigid polymeric material will be sufficiently thick so that, taken by itself, it can serve as a mechanical support and containment means for the medium contained by it. The thickness of the base polymeric substrate will necessarily depend on the structural configuration of the final device comprising the compositions, e.g. whether the device is a slab gel holder, capillary, microchannel, etc., as described in greater detail below, as well as the bulk properties of the base material, such as its tensile strength, brittleness, flexural strength, and the like. Generally, the thickness of the substrate will be at least about 0.25 mm, more usually at least about 0.5 mm and will generally not exceed about 10 mm, and will usually not exceed about 5 mm.

Polymeric materials suitable for use as the base material in at least the region of surface modification will be moldable and extrudable into a rigid objects that are electrically non-conductive, have high resistivity to electric fields and are stable in the presence of a variety of electrophoretic media under electrophoretic conditions, including aqueous solutions comprising high salt concentrations and having pH ranges from 2 to 12. The polymeric material may comprise one or more different polymers, but will usually comprise no more than four different polymers, more usually no more than two different polymers. The polymers may be homo- or copolymeric, and be uncrosslinked or crosslinked. Polymers finding use will be synthetic, usually organic and may be addition or condensation polymers. Polymeric materials from which electrophoretic chambers have been fabricated and are amenable to surface modification by the subject invention include: acrylics, e.g. polymethylmethacrylate; polycarbonate; polyethylene terepthalate; polystyrene; polyethylene; polypropylene; polyvinyl chloride; polyfluorocarbon; polybutylene terepthalate; polyvinyl alcohol; polyetherether ketone; polyamides or nylons; phenyl silicones; polyurethanes; acrylonitrile-styrene copolymers, copolymers of ethylmethacrylate and methylmethacrylate, and blends of polymethylmethacrylate and polyethylmethacrylate, and the like.

Depending on the particular device, as well as the detection method and system in which it is employed, it may be desirable for the polymeric material to be optically transparent, where optically transparent means that the material allows light of wavelengths ranging from 180 to 1500 nm, usually from 220 to 800 nm, more usually from 250 to 800 nm, to have low transmission losses. Such light transmissive polymeric materials will be characterized by low crystallinity and include polycarbonate, polyethylene terepthalate, polystyrene, polymethylpentene, fluorocarbon copolymers, and the like, as well as the acrylic polymeric materials described in co-pending application Ser. No. 08/627,484, the disclosure of which is herein incorporated by reference, with polyacrylates, particularly polymethacrylates, and more particularly polymethylmethacrylate (PMMA) being preferred materials.

In the region of surface modification, interpenetrating the internal surface of the electrophoretic chambers will be an anchoring polymeric layer. By interpenetrating is meant that the anchoring polymeric layer interdiffuses beneath the surface of the solid polymeric material. The interdiffused anchoring polymeric layer comprises linear polymeric strands, that may be either homopolymeric or copolymeric, extending throughout the region of the base material adjacent to the surface. In other words, in the interdiffused region there are linear polymeric strands intertwined throughout the base polymeric network, with substantially no grafting of the anchoring polymeric strands to the base polymeric strands. Since the method used to prepare the subject chambers requires a specific relationship between the base material and the monomer from which the anchoring polymeric layer is prepared (described in greater detail below), depending on the particular nature of the solid base polymeric material, the anchoring polymeric may be polymerized from one or more of a variety of different monomers, where the monomers will generally be addition polymerizable, usually vinylic, more usually non-oxo carbonyl, such as acrylic and pyrrolic, where the term acrylic includes methacrylic, where the acrylic monomers may be esters or amides. Specific anchoring polymers of interest are those polymerized from N-vinyl pyrrolidone, hydroxyethylmethacrylate, dimethyl acrylamide, hydroxymethylacrylamide, ethylene glycol dimethacrylate, glycerol methacrylate, glycidyl methacrylate, and the like, where polymers polymerized from dimethylacrylamide, N-vinyl pyrrolidone, hydroxymethylacrylamide and the like are preferable when the base polymeric material is polymethylmethacrylate. The distance to which the interdiffused portion of the base polymeric material extends beneath the surface of the base material will be a distance sufficient so that, when copolymerized with the surface electrophoretic layer, the interdiffused strands of the anchoring polymeric layer stably secure the surface electrophoretic layer to the base polymeric material surface. The interdiffused region of the base polymeric material will range in thickness from about 50 Å to 1500 Å, usually from about 30 Å to 700 Å and more usually from about 15 Å to 500 Å. There will be no sharp demarcation at the border defining the extent of the interdiffused anchoring polymeric layer.

The electrophoretic layer stably secured to the surface of the base material in the region of surface modification can serve to impart a number of different properties to the surface, including changing the inherent surface charge of the chamber, providing for reactive functional groups, providing for an electrophoretic medium that substantially fills the inner volume of the chamber, and the like. Although the electrophoretic layer may be polymerized from a variety of different monomeric compounds depending on the purpose of the layer, it will be polymerized from addition polymerizable monomers capable of copolymerization with the interpenetrated monomers of the anchoring layer.

By changing the surface charge characteristics of the base polymeric material, the electrophoretic layer can serve a variety of purposes, including enhancing or reducing the occurrence of EOF in the chamber, providing for enhancement, reduction or selectivity in entity adsorption to the surface of the chamber, etc. For example, an electrophoretic layer polymerized from appropriate monomers can be employed in order to mask or cover any surface charge inherent in the solid polymeric base material under conditions of electrophoresis. By masking the surface charge, one can substantially reduce or eliminate the occurrence of EOF during electrophoresis. Electrophoretic layers which are suitable for at least reducing if not substantially eliminating the occurrence of EOF include those hydrophilic polymers having uncharged side groups, where the side groups may be amides, esters, pyrroles, hydroxides and the like. Specific electrophoretic layers providing for reduced EOF include: polyacrylamide and polymethacrylamide, polyhydroxyethylmethacrylate, polyvinylpyrrolidone, polyhydroxymethylacrylamide and the like. One could also enhance the magnitude of the EOF, or reverse the direction of the EOF, by having an electrophoretic layer polymerized from monomers comprising charged groups of the same charge as the surface charge of the chamber. By selection of an electrophoretic layer polymerized from monomers having appropriately charged groups, one can also provide for a reversal in the direction of EOF through the chamber. Charged groups of interest that may be present in the electrophoretic polymeric layer include carboxylic, sulfonic, phosphoryl, amine, and the like, where specific electrophoretic layers finding use in the enhancement or reversal of EOF include carboxylic, sulfonic, amine, and the like.

Instead of, or in addition to, changing the EOF in the chamber during electrophoresis, the electrophoretic layer can provide for a reduction, including a substantial elimination, of the adsorption of biomolecules-to the surface of the chamber. To accomplish a reduction in the adsorption of biomolecules to the chamber surface, the electrophoretic layer can be provided that comprises hydrophilic groups having no net electrical charge, where such groups include both neutral groups such as those described above, e.g. polyacrylamide, copolymers of polyethyleneglycol acrylates of molecular weight lower than 1000 dal, and polymers comprising zwitterionic groups, such as alanyl, betaine, sulfobetaine and choline derivatives, and the like. Alternatively, one could enhance the adsorption of entities to the surface of the chamber, as well as provide for the selective adsorption of a particular class of entities, through the presence of the electrophoretic layer. Specific electrophoretic layers for reducing surface adsorption include polyacrylamide while specific electrophoretic layers for enhancing surface adsorption include polyacrylamide-2-methylpropane sulfonic acid.

The electrophoretic layer may also provide for the presence of a variety of reactive functional groups on the surface of the chamber in the region of modification, such as hydroxy, amino, epoxy, carboxy, amide, isocyanate, aldehyde, sulfonic and the like. By appropriate choice of monomer or monomers, the electrophoretic layer can provide for a single type of functional group or a plurality of different functional groups in the region of the surface modification. The presence of reactive functional groups on the surface of the chamber can be useful where it is desired to covalently bond agents to the surface, e.g. enzymes, proteins, antibodies, dies, pH modifiers, complexing agents, etc. For example, for the covalent attachment of proteins comprising primary or secondary amino groups, an electrophoretic layer comprising epoxide and aldehyde groups will be of interest. Specific electrophoretic polymeric materials of interest comprising reaction functional groups include: copolymers of glycidyl methacrylate and acrolein and the like.

The electrophoretic layer can also serve as an electrophoretic medium through which entities are moved in electrophoretic applications, where the electrophoretic layer is capable of providing for electrophoretic sieving as the entities move through the medium under the influence of the applied electric field. In this embodiment of the subject invention, the electrophoretic layer will substantially fill the entire inner volume of the electrophoretic chamber, at least in the volume bound by the region of surface modification, where the layer may comprise crosslinked and/or non-crosslinked polymers. Polymeric gel media suitable for use in electrophoresis are disclosed in Barron & Blanch, Separation & Purification Methods, (1995) 24:1–118. Specific electrophoretic layers capable of serving as electrophoretic layers are those polymerized from addition polymerization, and are usually vinylic, more usually acrylic, with polyacrylamides being preferred. Also of interest in certain applications, e.g. preparative applications, are gels comprising reactive groups, such as amino groups, sulfonic groups, and the like.

The subject electrophoretic chambers may have a variety of different configurations. Chambers having walls capable of being modified according to the subject invention include slab gel chambers, tubes, columns, as well as microchannel chambers, such as capillaries and trenches on the surface of planar polymeric substrate. As discussed above, the entire inner surface of the chamber may be modified to comprise the electrophoretic layer, or only a region of the inner surface may be so modified. In addition, the chambers may comprise one or more regions of surface modification, where when a plurality of regions of surface modification are provided, one has the opportunity to have a plurality of different electrophoretic layers on the surface of the chamber, which increases the variety of different applications in which the chambers may be used. For example, a chamber could be prepared having a first region in which the electrophoretic layer is a gel containing an ionically charged group, e.g. carboxy, sulfonic, amino etc., that provides for ion exchange. Downstream from the first region could be a second region comprising an enzyme that converts a sample component to a desired product. Downstream from the second region could then be a third region modified to comprise an electrophoretic sieving medium, e.g. cross linked polyacrylamide, in which the enzyme product is separated from the remaining sample components.

One embodiment of particular interest is where the electrophoretic chamber is a microchannel. The microchannels may be open or closed, where by "open" is meant that the internal volume of the microchannel is not completely separated on at least one longitudinal side from the external environment, while by "closed" is meant that the internal volume of the channel is completely separated longitudinally from the external environment. Examples of open microchannels include troughs, trenches and the like, present on the surface of a planar substrate, while closed channels are exemplified by cylinders, tubes, capillaries and the like. The subject microchannels will have micro scale cross-sectional inner dimensions, such that the inner cross-sectional dimensions of the microchannels will be greater than 1 $\mu$m and less than 1000 $\mu$m. Generally, the cross-sectional inner dimension(s) of the microchannel, i.e. width, depth or diameter depending on the particular nature of the channel, will generally range from about 1 to 200 $\mu$m, usually from about 10 to 150 $\mu$m, more usually from about 20 to 100 $\mu$m, with the total inner cross sectional area of the microchannel providing for capillary flow through the channel, and ranging from about 100 to 40000 $\mu$m$^2$, usually from about 400 to 25,000 $\mu m^2$. The inner cross-sectional shape of the microchannel may vary among a number of different configurations, including rectangular, square, rhombic, triangular or V-shaped, circular, semicircular, ellipsoid and the like. The length of the microchannel will necessarily depend on the specific nature of the vessel as well as the electrophoretic device in which it is to be employed. For example, where the microchannel is a trough or trench in a substrate, the length of the microchannel may range from about 0.1 to 100 cm, and will generally range from about 1 to 20 cm, usually from about 1 to 10 cm, and more usually from about 5 to 10 cm, while for capillaries the length will generally range from about 10 to 100 cm, usually from about 10 to 75 cm, more usually from about 20 to 50 cm. Where the subject microvessel is contained within a capillary, the thickness of the wall of the capillary may range from about 50 to 1000 $\mu m$, usually from about 100 to 500 $\mu m$, more usually from about 100 to 150 $\mu m$, to provide a capillary with an outer diameter ranging from about 100 to 2000 $\mu m$, usually from about 150 to 400 $\mu m$.

Where the microchannel is a trench or trough extending downward from the surface of a substrate, conveniently a groove in the substrate, the substrate may be square, rectangular, circular and the like, and will have dimensions which will vary considerably depending on the intended use of the microchannel. Where the substrate has card-like or substantially regular parallelepiped dimensions, the length of the substrate will typically range from about 2 to 200 mm, the width of the substrate will typically range from about 2 to 200 mm, while the thickness of the substrate will typically range from about 0.1 to 10 mm. One or more, usually at least 2 and up to 100 or more, microchannels may be present on or at the surface of the substrate, where when a plurality of microchannels are present at the substrate surface, the possibility exists to have a number of different electrophoretic applications running at the same time on a single substrate. The microchannel(s) present in the substrate surface can be linear, branched or in some other convenient configuration. With branched microchannels or trenches, the possibility exists to have a first trench or channel intersected by one or more side channels, where the side channels may intersect the main channel at any convenient angle. In branched configurations, the chamber will comprise a main microchannel in intersecting relationship with at least one secondary microchannel, where at least one pair of electrodes will be associated with each microchannel, with one member of the pair being positioned at either of the termini of the channel, in order to apply an electric field to the medium in the microchannel. See U.S. Pat. No. 5,126,022, the disclosure of which is herein incorporated by reference.

As the microchannel(s) present on the substrate surface may be open, it may be desirable to separate the internal volume of the channel, and thereby the medium housed in the channel, from the external environment. In such instances a cover plate can be employed which rests on the surface of the substrate and thereby separates the internal volume of the channel from the environment. The cover plate may be fabricated from a number of different materials, including fused silica, acrylic polymeric materials, and the like. Where necessary and desirable, one or more of the cover plate surfaces may be treated to reduce any EOF that may arise during electrophoresis. A number of different methods are known which reduce or eliminate EOF. Alternatively, where the cover plate is a rigid polymeric material, the method of the subject invention can be employed to appropriately modify the surface. As with the substrate, the coverplate may be fabricated from a single type of material or be a composite of one or more, usually two, materials.

The thickness of the cover plate will usually range from about 0.01 to 10 mm, more usually from about 0.1 to 1.0 mm, where the length and width of the cover plate may be similar to, or different from, the length and width of the substrate, but will usually be substantially the same as those of the substrate. The cover plate may have substantially smooth, planar, flat surfaces, or optionally may be a mirror image of the substrate. Although not necessary, the cover plate will generally be sealed to the substrate. The cover plate and substrate may be sealed using any convenient means, such as ultrasonic welding, pressure, thermoprocessing, adhesives, sealants, physical conformance and the like.

The electrophoretic chambers can be used in a variety of electrophoretic devices. Numerous electrophoretic devices are known in the art, and include both devices which require manual operation as well as automated devices requiring a minimal amount of operator interaction. The electrophoretic chambers of any of these devices can be substituted with the subject electrophoretic chambers of analogous configuration.

In preparing the subject electrophoretic chambers, the base polymeric layer is contacted sequentially with first and second monomer compositions which are then subsequently copolymerized to produce the region of surface modification. Copolymerization with the first and second monomers will be through addition polymerization, with the first and second monomers being olefinic, usually vinylic monomers, where at least the second monomer will be different from the monomer(s) from which the base polymeric material is polymerized, where the first and second monomers may be the same or different and are usually different, so that at least the electrophoretic layer differs from the rigid polymeric base material. In those select situations where the first and second monomers are the same, the two step process of the subject invention allows one to interpenetrate the first monomer in a first solvent which promote interpenetration, and then polymerize the first and second monomers in a solvent that is particularly suited for polymerization. As the first and second monomers are copolymerized and are usually different, the kinetic copolymerization relationship between the first and second monomers will lie between ideal and alternating, i.e. $0<r_1r_2<1$, where the relationship will be closer to ideal, with $r_1r_2$ usually being between 0 to 2, more usually between 0 and 1.

The first step is to contact the region to be modified with a first monomer capable of interpenetrating the surface. In interpenetrating the surface of the base polymeric material, the first monomer swells the surface of the base polymeric material and incorporates or becomes embedded beneath the surface of the material, where it positions itself among the polymeric strands of the base material. The distance to which the first monomer penetrates below the surface of the base material will be at least about 15 Å, usually at least about 30 Å and may be as great as about 1500 Å or greater, but will usually not exceed about 500 Å. Although the first monomer swells the surface of the polymeric material through interpenetration, because the interdiffused region only extends to at most a few nanometers below the surface of the layer, the bulk properties of the material, such as water solubility or rigidity will not be changed as a result of interpenetration.

Because the first monomer must be capable of penetrating the surface of the base polymeric material, the first monomer employed will be chosen in view of several different considerations, including: (a) the particular chemical structure and physical morphology of the polymeric base material; (b) the similarity in the solubility parameters between the first monomer and the base polymeric material; (c) the nature of the electrophoretic layer with which it is to be copolymerized; and the like. For acrylic polymeric base materials, e.g. polymethacrylates, first monomers that find use include vinylic monomers, particularly non-oxo carbonyls, particularly N comprising non-oxo carbonyls where the carbonyl is directly bonded to the N, where the N may be annular and substituted, either mono- or di-substituted, where substituents will generally be lower alkyls, usually C4 or lower, more usually C2 or lower, particular methyl, with acrylic and pyrrolic monomers being of interest, with specific monomers of interest being dimethylacrylamide, N-vinyl pyrrolidone, methyl methacrylate and the like.

In contacting the first monomer with the base polymeric material, the first monomer may be present as a pure liquid or in a solvent, where the solvent preferably promotes the swelling of the surface of the base material and the interpenetration of the first monomer. Thus, the solvent will also generally have a similar solubility parameter to that of the base material. For acrylic base materials, solvents of interest include lower alkanols, such as methanol, isopropanol and the like. Where the first monomer is present in a solvent, the first monomer will typically be present in an amount ranging from about 1 to 100% by volume, usually from about 3 to 75% by volume, and more usually from about 3 to 50% by volume. Contact may be accomplished under dynamic or static conditions, as is convenient. Under dynamic conditions, the first monomer or solution thereof will be moved through the chamber at a flow rate that ranges from about 10 $\mu$l/min to 5 ml/min, more usually from about 25 $\mu$l/min to 3 ml/min The parameters of the contacting step will be selected to achieve the desired level of surface swelling and interpenetration of the first monomer without comprising the bulk mechanical properties of the base polymeric material. Parameters that will be chosen accordingly include duration of contact, nature of solvent, concentration of monomer in solvent, temperature and the like. Contact will generally be maintained for a period of time ranging from about 0.25 to 4 hr, usually from about 0.5 to 2 hr, and more usually from about 0.5 to 1 hr. After sufficient time has elapsed for the first monomer to interpenetrate the polymeric surface, excess first monomer will be removed from the surface. The excess first monomer may be removed using any convenient means, such as wiping, washing, flushing nitrogen or air under pressure and the like.

The next step in the subject method is to contact the interpenetrated or interdiffused surface of the base material with a second monomer composition. The second monomer will be copolymerizable with the first monomer through addition polymerization, and will usually be vinylic. The vinylic second monomer will comprise a moiety which imparts the particular surface modification characteristics to the electrophoretic layer into which it is polymerized. For electrophoretic layers that modify the inherent surface charge of the base material under conditions of electrophoresis, the second monomer will be hydrophilic and can comprise neutral or charged groups, depending on the purpose of the electrophoretic layer. Where the electrophoretic layer is to reduce or eliminate the occurrence of EOF through the chamber during electrophoresis, second monomers that find use include those monomers having neutral hydrophilic groups, such as non-oxo carbonyls, including acrylic and pyrrolic monomers, where acrylic monomers may be esters or amides. Specific second monomers of interest for use in the reduction of EOF include: acrylamide, hydroxyethylmethacrylate, vinyl pyrrolidone, end-capped polyethylene glycol acrylates of molecular weight lower than 1000, and zwitterionic monomers such as the betaine derivatives, and the like. For enhancing the magnitude of, or reversing the direction of, EOF through the chamber, the second monomer can be a monomer comprising a charged group, where the charged group can be negative or positive, where negatively charged groups include carboxylic groups, sulfonic groups, phosphoryl groups, and the like, as found in monomers such as vinylic acids, e.g. acrylic acid, methacrylic acid, and the like, while positively charged groups include amino, and the like, as found in 2-(dimethylamino)ethyl acrylate, 2-(diethylamino) ethyl ethacrylate and the like.

Where the electrophoretic layer is introduced to reduce the adsorption of entities to the surface of the chamber, second monomers of interest include: the neutral group comprising hydrophilic monomers listed above, e.g. acrylamide, hydroxyethylmethacrylate, dimethylacrylamide, vinyl pyrrolidone, low molecular weight (less than 1000 dal) polyethylene glycol acrylates, and the like; zwitterionic groups having an overall net charge of zero, such as N-(3-sulfopropyl)-N-methacryloxyethyl-N,N-dimethyl ammonium betaine, and the like; as well as polyethylene glycol acrylates of low molecular weight, and the like.

For electrophoretic layers comprising reactive functional groups, the second monomer will comprise a moiety which is the functional group. For the immobilization of an affinity agent to the surface of the chamber, reactive functional groups that provide covalent bonding to the affinity agent are of interest. Different methodologies employing a variety of different functional reactive groups for the immobilization of affinity agents to the surface of polymeric substrates are known. See Trevan, "Immobilized Enzymes, An Introduction and Applications in Biotechnology," (J. Wiley & Sons, 1980), Protein Immobilization, Fundamentals and Applications, (ed. Taylor & Dekker)(1991); and Walsh & Headon, "Protein Biotechnology" (J. Wiley & Sons)(1994), the disclosures of which are herein incorporated by reference. Reactive functional groups of interest which can either react directly with an affinity agent or be treated to provide for groups capable of directly reacting with affinity agents include hydroxy, amino, epoxy, carboxy, amide, isocyanate, aldehyde and the like. Specific second monomers of interest include glycidyl methacrylate, acrolein and the like.

Where the surface electrophoretic layer is to substantially fill the inner volume of the chamber to provide for an electrophoretic medium, where the medium may comprise linear or crosslinked polymeric networks, second monomers of interest include acrylamide, dimethylacrylamide, other monosubstituted and disubstituted acrylamides, and the like.

The second monomer will be present in a solution, where a variety of solvent systems may be employed, including co-solvent systems. Solvent systems of interest include pure water and water/lower alkanol mixtures, where the lower alkanol will typically be a C4 or lower alkanol, such as ethanol, propanol, isopropyl alcohol and the like. Instead of, or in addition to, a lower alkanol, other polar organic solvents may be employed as co-solvents, such as dimethylformamide, dimethylsulfoxide and the like. The volume percent of the water in the solvent system will range from 10 to 100%. The volume percent of the co-solvent in the system, when present, will not exceed 90%, and will usually not exceed 50%. Non-aqueous solvent systems may also be employed, where the non-aqueous solvents may be selected from any convenient organic solvent, such as those listed above. The volume percent of second monomer in the solvent will generally range from about 3 to 20%, usually from about 3 to 12% and more usually from about 3 to 8%.

In addition, the second monomer solution may further comprise various agents necessary and/or desirable for the polymerization, where such agents include those agents useful in physical and chemical initiation. Chemical initiators include: persulphate+3-dimethylaminopropionitrile (DMPAN), persulphate+tetramethylethylenediamine (TEMED), persulphate, persulphate+thiosulfate, persulphate+bisulfite, persulphate+ diethylmethylaminediamine (DEMED), $H_2O_2+Fe^{2+}$, benzoyl peroxide, lauroyl peroxide, tetralin peroxide, actyl peroxide, caproyl peroxide, t-butyl hydroperoxide, t-butyl perbenzoate, t-butyl diperphthalate, cumene hydroperoxide, 2-butanone peroxide, azoinitiators, e.g. azodiisobutyronitrile and azodicarbonamide, riboflavin, methylene blue+a redox couple, and the like. Preferably a chemical polymerization initiator such as persulphate will be employed.

For the preparation of cross-linked electrophoretic layers, the second monomer composition may further comprise various cross linking agents, which will be selected depending on the nature of the second monomer. For example, with acrylic monomers, e.g. acrylamide, cross linking agents of interest include: N,N'-ethylene bisacrylamide (Bis); ethylene diacylate (EDIA); N,N'-diallyltartardiamide (DATD); N,N'-bis acrylyl cystamine (BAC); N,N'-(1,2-dihydroxyethylene)bisacrylamide (DHEBA); and the like. Other agents of interest that may be present for a variety of reasons in the composition, e.g. to provide for suitable electrophoretic sieving through the layer polymerized from the composition, include various salts, particularly buffering salts, where the concentration of the buffering salts will vary from 0.01 to 0.5, more usually from 0.01 to 0.1 M. The salts may include Tris, phosphate, EDTA, MOPS, and the like. Denaturing agents may also be present in the aqueous phase, including urea, SDS, formamide, methylmercuric hydroxide, alkali, and the like, where the concentration will vary depending on the particular denaturing agent, e.g. for urea, the concentration will range from about 0.1 to 9.0 M.

Following contact of the second monomer composition with the interpenetrated surface, the first and second monomers will be copolymerized. Depending on the particular second monomer composition, polymerization may already have been initiated upon preparation of the second monomer composition, e.g. where a chemical initiator such as persulphate is employed. Where polymerization is not initiated upon preparation of the second monomer composition, polymerization may then be initiated once contact is made using any convenient means, including heat, electron beam, photopolymerization, gamma radiation, microwave radiation, and the like. However, the particular polymerization technique employed will be chosen so that little or no grafting of the base polymeric material occurs during copolymerization of the first and second monomers.

Upon initiation of the polymerization in the second monomer composition, as the polymer chain extends through the second monomer composition, those second monomers near the interpenetrated surface react with the first monomers embedded in the material near the surface, which then react with first monomers further below the surface, whereby the growing polymer chain continues to extend below the surface through the interdiffused region of the polymer, adding embedded first monomers to the growing chain.

Contact of the second monomer with the surface may be either static or dynamic, depending on the desired properties of the electrophoretic layer. For example, static conditions will be employed to obtain a thick electrophoretic layer, such as those electrophoretic layers that are to serve as a gel medium. Alternatively, dynamic conditions can be employed to achieve a thinner electrophoretic layer having a more uniform surface comprising lower molecular weight networks, which may be desirable for those applications where the electrophoretic layer is to alter the inherent surface charge of the material or to provide for the introduction of certain functional groups on the surface of the material in the region of modification. Where dynamic conditions are employed for contact, the flow rate of the second monomer composition through the chamber will typically range from 10 $\mu$l/min to 5 ml/min, usually from about 25 $\mu$l/min to 3 ml/min, and more usually from about 50 $\mu$l/min to 3 ml/min.

Polymerization will be allowed to continue for sufficient time for an electrophoretic layer of desired properties to be produced, and will generally be allowed to proceed to completion. Although the exact time will vary depending on the particular nature of the system employed, usually polymerization will proceed from about 0.25 to 4 hr, usually from about 0.5 to 2 hr, and more usually from about 0.5 to 1 hr.

Following polymerization, the surface modified chamber may be further treated as necessary, depending on the electrophoretic application in which it is to be employed. For example, where the electrophoretic surface is a gel medium, the fluid phase of the gel medium may be replaced with a running buffer. Alternatively, where the electrophoretic layer comprises functional groups for covalent attachment of affinity agents such as ligand or receptors, the modified surface may be contacted with such affinity agents, and then washed to remove any unbound agents.

The subject electrophoretic chambers find use in a variety of electrophoretic applications, where by electrophoretic applications is meant that charged entities are moved through a medium housed in a chamber under the influence of an applied electric field, where movement of the entities may be the result of either an inherent electrical charge of the entities or bulk fluid flow through the chamber. Illustrative applications are reviewed in Andrews, Electrophoresis (1990); Barron & Blanch, Separation & Purification Methods (1995) 24:1–118 and U.S. Pat. No. 5,126,022, the disclosures of which are herein incorporated by reference. Illustrative applications include methods based on sample component separation and identification, e.g. sequencing, sample component purification, synthesis applications, sample preparation and the like.

The following examples are offered by way of illustration and not by way of limitation.

EXPERIMENTAL

Example 1

Preparation of Cross-linked Polyacrylamide Gel Bound Between Two Polymethacrylate Plates and Its Use in the Electrophoretic Separation of a ΦX174/HaeIII DNA Ladder Flat polymethylmethacrylate (PMMA) plates 160×180 mm were cut from an Acrylite OP4 acrylic sheet (Cyro Industries). The plates were stringently wiped with methanol to ensure that no particles or residues were left on the surface of the plates. 10 mL of 10% dimethylacrylamide (DMA) in methanol were pipetted onto the surface of each plate. The DMA solution was gently spread using a lab paper tissue to cover the entire surface of the plates. The DMA solution was allowed to penetrate the surface of the plates for 20 minutes. After 20 minutes, the DMA solution was wiped clean using a lab paper tissue and lightly flushed with nitrogen gas. The surface was then wiped with a lab paper tissue wetted with methanol, resulting in a clear and spotless surface. 21.5 g of T5C3 (1 g of acrylamide, 35 µg of bisacrylamide and 20.5 g water) was combined with 1.0 g 10×TBE (0.89 M tris (hydroxymethyl)aminomethane, 0.89 M boric acid and 0.05 M ethylenediaminetetraacetic acid) and 2.2 µl 25 mM ethidium bromide solution. 150 µl 10% ammonium persulfate solution and 75 µl TEMED were added to the above solution and mixed gently. The resultant solution was poured between the two treated PMMA surfaces separated by 75 µm spacers and allowed to polymerize for about two hours. A well forming comb was introduced between the plates to form sample wells for electrophoresis.

The resultant cross-linked polyacrylamide gels had good adhesion to the PMMA plates as a result of the surface treatment. In contrast, cross-linked gels poured between two PMMA plates having untreated surfaces slid out of the plates upon removal from the casting stand.

Electrophoresis of ΦX174/HaeIII DNA fragments was performed using standard procedures with a run voltage of 7.4 V/cm for 2.25 hours. The results were visualized on a standard UV imaging system.

The non-denaturant separation of ΦXI74/HaeIII DNA fragments under these conditions resolved 8 bands of the 11 possible fragments resolvable under more ideal conditions. The experiment was designed to demonstrate the resolving capacity of the gel while being attached to the surface of the PMMA plates using the described method.

The results demonstrate that the surface interpenetration method according to the subject invention can be used to stably secure and electrophoretic gel medium to the surface of a polymethylmethacrylate plate and the such a secured gel can be used successfully in electrophoretic separation.

Example 2

Preparation of Polymethylmethacrylate Capillaries Having an Inner Linear Polyacrylamide Coating The inner surface of a cleaned microbore polymethylmethacrylate capillary is contacted with a 10% solution of dimethylacrylamide (DMA) in methanol for 20 minutes under static conditions. After 20 minutes, the excess DMA solution is rinsed from the internal capillary surface and a fresh solution of 3% acrylamide in water with ammonium persulfate and N,N,N,N-tetramethylenediamine (TEMED) is introduced into the internal volume of the capillary. The 3% acrylamide solution is maintained in the capillary for two hours at room temperature under static conditions, allowing for copolymerization of the linear acrylamide with DMA monomers that penetrated the surface of the capillary wall. Since the copolymerization is carried out under static conditions, the linear polyacrylamide strands grow into a thick intertwining network that essentially fills the entire volume of the capillary. The resultant linear acrylamide filled polymethylmethacrylate capillary can be used in electrophoretic separation applications.

The above procedure is also carried out with the variation that the acrylamide solution is introduced into the capillary under dynamic conditions, with a flow rate of 3 ml/min. Introducing the acrylamide solution under dynamic conditions results the formation of a thin linear acrylamide layer covering the surface of the capillary.

Example 3

Preparation of Polymethylmethacrylate Capillaries Having an Inner Surface Comprising Epoxy Functional Groups A PMMA capillary having a DMA interpenetrated surface is contacted with a solution of glycidyl methacrylate comprising t-butyl peroxypyvalate (TBPP) under dynamic conditions, e.g. the glycidyl methacrylate is flowed through the chamber at a rate of 50 µl/min at 40° C. Copolymerization results in the presence of a thin, uniform surface polymeric layer comprising epoxy groups. The epoxy groups can then be converted to other functional groups, as may be appropriate depending on the use of the functional group, e.g. to hydroxy groups through acid hydrolysis.

Example 4

Preparation of Polymethylmethacrylate Capillaries Comprising Ion Containing Cross-linked Gels A. Capillaries Filled with Amine Containing Gel Structures A polymethylmethacrylate capillary is filled with a 20% solution of methylmethacrylate in methanol under static conditions for 30 min. The capillary is then rinsed and a fresh 15% solution of dimethylaminoethylacrylate in methanol containing 5% ethylene glycol diacrylate and 1% t-butyl peroxypyvalate (TBBP) is introduced into the capillary. Polymerization is allowed to proceed for 2 hr at 40° C. The resultant capillary is substantially filled with an amino containing gel structure which finds use anion exchange applications, e.g. ion removal in high ionic strength samples.

B. Capillaries Filled with Sulfonic Acid Containing Gel Structures

An MMA surface interpenetrated PMMA capillary as prepared in A. above is contacted with a 20% solution of 2-acrylamido-2-methylpropanesulfonic acid comprising 5% N,N'-ethylene bisacrylamide and 0.15% of persulfate/bisulfate in water containing 10% sodium hydroxide (pH adjusted to 7–8) under static conditions. Polymerization is allowed to proceed for 1 hr at 55° C. with careful control of the temperature of the bath. The resultant capillary comprises a sulfonic acid containing gel structure which finds use in cation exchange applications, e.g. ion removal in high ionic strength samples.

It is evident from the above results and discussion that the subject invention provides a powerful methodology for the tailoring of the surface properties of an electrophoretic chamber to best suit the needs of a particular application. With the subject invention, electrophoretic mediums stably secured to the surface of the chamber material can be fabricated. Furthermore, one can readily control the nature of the functional groups introduced on the surface, providing for a homogenous surface where desired. With the subject methodology one can also provide for a tailored surfaces having a plurality of regions of different modification, which greatly increases the number and nature of applications in which the subject chambers can be employed.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An electrophoretic chamber comprising at least a region of surface modification, wherein said region comprises:
   a rigid polymeric base material;
   an anchoring polymeric layer interpenetrating the surface of said base material; and
   a polymeric electrophoretic layer copolymerized to said anchoring polymeric layer.

2. The chamber according to claim 1, wherein said rigid polymeric base material is acrylic.

3. The chamber according to claim 1, wherein said chamber is a capillary.

4. The chamber according to claim 1, wherein said chamber comprises a main microchannel on the surface of a planar substrate.

5. The chamber according to claim 4, wherein said chamber further comprises at least one secondary microchannel in intersecting relationship with said main microchannel.

6. The chamber according to claim 1, wherein said chamber comprises a plurality of said regions.

7. The chamber according to claim 1, wherein said surface polymeric electrophoretic layer is a gel electrophoretic medium which substantially fills the internal volume of said chamber.

8. The chamber according to claim 1, wherein said electrophoretic layer comprises a moiety capable of changing the surface charge of said chamber in said region.

9. The chamber according to claim 1, wherein said electrophoretic layer comprises a reactive functional group.

10. The chamber according to claim 2, wherein said acrylic substrate is polymethylmethacrylate.

11. An electrophoretic chamber comprising at least one region of surface modification, wherein said region comprises:
    a rigid acrylic material;
    an anchoring acrylic polymeric layer interpenetrating the surface of said rigid acrylic material; and
    a polymeric electrophoretic layer copolymerized with said anchoring polymeric layer,
    wherein at least one of said anchoring and electrophoretic layers differs from said rigid acrylic material.

12. The chamber according to claim 11, wherein said chamber is a main microchannel on a planar substrate.

13. The chamber according to claim 12, wherein said chamber further comprises at least one secondary microchannel in intersecting relationship with said main microchannel.

14. The chamber according to claim 11, wherein the surface of said chamber comprises a plurality of said regions.

15. The chamber according to claim 11, wherein said surface polymeric electrophoretic layer is an electrophoretic gel medium which substantially fills the inner volume of said chamber.

16. The chamber according to claim 11, wherein said polymeric electrophoretic layer changes the surface charge of said chamber in said region.

17. The chamber according to claim 11, wherein said polymeric electrophoretic layer comprises reactive functional groups.

18. The chamber according to claim 17, wherein said region further comprises an agent covalently bound to said electrophoretic layer.

19. The chamber according to claim 18, wherein said agent is an enzyme, receptor or ligand.

20. A device comprising an electrophoretic chamber comprising at least a region of surface modification, wherein said region comprises:
    a rigid polymeric base material;
    an anchoring polymeric layer interpenetrating the surface of said base material; and
    a polymeric electrophoretic layer copolymerized to said anchoring polymeric layer.

21. The device according to claim 20, wherein said device further comprises an electrophoretic medium in said chamber.

22. A device for use in an electrophoretic application in which entities are moved through a medium in response to an applied electric field, said device comprising an electrophoretic chamber according to claim 11.

23. The device according to claim 22, wherein said device further comprises an electrophoretic medium in said chamber.

24. A method for making a polymeric electrophoretic chamber comprising at least one region of surface modification, said method comprising:
    contacting the surface of a rigid polymeric base material in said region with a first monomer capable of interpenetrating said surface to produce an interpenetrated surface;
    contacting said interpenetrated surface with a second monomer capable of copolymerizing with said first monomer; and
    copolymerizing said first and second monomers to produce said electrophoretic chamber.

25. The method according to claim 24, wherein said rigid polymeric material is organic.

26. The method according to claim 25, wherein said organic rigid polymeric material is acrylic.

27. The method according to claim 24, wherein said method comprises performing said contacting and copolymerization steps a plurality of times to produce an electrophoretic chamber comprising a plurality of said regions.

28. A method for making a polymeric electrophoretic chamber comprising at least one region of surface modification, said method comprising:
    contacting the surface of a polymethylmethacrylate base material in said region with a first acrylic monomer capable of interpenetrating said surface to produce an interpenetrated surface;
    contacting said interpenetrated surface with a second monomer capable of copolymerizing with said first monomer; and
    copolymerizing said first and second monomers to produce said electrophoretic chamber.

29. The method according to claim 28, wherein said method further comprises initiating said copolymerization.

30. The method according to claim 28, wherein said second monomer is selected from the group consisting of dimethyacrylamide, methylmethacrylate and N-vinyl pyrrolidone.

31. The method according to claim 30, wherein said second monomer comprises a moiety having a reactive functional group and said method further comprises covalently bonding an affinity group to said moiety.

32. In a method of electrophoresis in which entities are moved through a medium by applying an electric field to said medium, the improvement comprising:
    employing the device according to claim 20.

33. The method according to claim 32, wherein said method is a method of separating said the components of a sample.

34. The method according to claim 33, wherein said components are charged.

35. A device comprising:

a rigid polymeric material having a first surface comprising at least one microchannel;

a first polymeric layer interpenetrating said first surface; and a second polymeric material copolymerized with said first polymeric layer.

36. The device according to claim 35, wherein said rigid polymeric material is acrylic.

37. The device according to claim 36, wherein said rigid polymeric material is polymethyl methacrylate.

* * * * *